United States Patent [19]

Euteneuer

[11] Patent Number: 5,195,989

[45] Date of Patent: Mar. 23, 1993

[54] LOW PROFILE CATHETER FOR INCREASING LUMEN SIZE OF A BLOOD VESSEL AND GUIDE WIRE THEREFOR

[75] Inventor: Charles L. Euteneuer, St. Michael, Minn.

[73] Assignee: Scimed Life Systems, Inc., Maple Grove, Minn.

[21] Appl. No.: 583,437

[22] Filed: Sep. 17, 1990

[51] Int. Cl.$^5$ .......................................... A61M 25/00
[52] U.S. Cl. ........................................ 604/280; 604/96
[58] Field of Search .................. 604/96, 97, 98, 99, 604/165, 264, 22; 600/18; 128/772, 656–658; 606/192

[56] References Cited

U.S. PATENT DOCUMENTS

| | | | |
|---|---|---|---|
| 2,819,718 | 1/1958 | Goldman | 604/96 |
| 4,004,588 | 1/1977 | Alexander | 128/241 |
| 4,166,468 | 9/1979 | Haynie | 128/351 |
| 4,413,989 | 11/1983 | Schjeldahl et al. | 604/96 |
| 4,580,573 | 4/1986 | Quinn | 128/657 |
| 4,582,181 | 4/1986 | Samson | 128/348.1 |
| 4,606,347 | 8/1986 | Fogarty et al. | 128/344 |
| 4,616,653 | 10/1986 | Samson et al. | 128/344 |
| 4,641,654 | 2/1987 | Samson et al. | 128/344 |
| 4,646,742 | 3/1987 | Packard et al. | 128/344 |
| 4,696,667 | 9/1987 | Masch | 604/22 |
| 4,721,117 | 1/1988 | Mar et al. | 128/772 |
| 4,743,647 | 5/1988 | Domeier | 524/516 |
| 4,771,778 | 9/1988 | Mar | 128/344 |
| 4,793,350 | 12/1988 | Mar et al. | 128/344 |
| 4,827,941 | 5/1989 | Taylor et al. | 128/657 |
| 4,838,268 | 6/1989 | Keith et al. | 128/344 |
| 4,841,976 | 6/1989 | Packard et al. | 128/657 |
| 4,875,489 | 10/1989 | Messner et al. | 128/772 |
| 4,917,103 | 4/1990 | Gambale et al. | 128/772 |
| 4,917,666 | 4/1990 | Solar et al. | 604/95 |
| 4,922,923 | 5/1990 | Gambale et al. | 128/772 |
| 4,932,413 | 6/1990 | Shockey et al. | 128/657 |
| 4,932,959 | 6/1990 | Horzewski et al. | 604/165 |
| 4,934,380 | 6/1990 | de Toledo | 128/772 |
| 5,045,061 | 9/1991 | Seifert et al. | 604/96 |
| 5,055,109 | 10/1991 | Gould et al. | 604/95 |

Primary Examiner—C. Fred Rosenbaum
Assistant Examiner—M. Mendez
Attorney, Agent, or Firm—Willian Brinks Olds Hofer Gilson & Lione

[57] ABSTRACT

A low profile catheter for increasing lumen size of a blood vessel includes a catheter shaft which carries an inflatable balloon at its distal end. A guide wire is positioned in the catheter shaft to extend beyond the balloon, and the guide wire defines a keyed portion having a cross-sectional shape which is other than round. A keyed coupling number is carried by the catheter shaft and coupled to the keyed portion of the guide wire to transmit torque from the catheter shaft to the guide wire while permitting relative axial movement between the catheter shaft and the guide wire. Alternately, wound coil springs are mounted to the catheter shaft by a spyder. The coil springs seize the guide wire in response to rotation, but allow longitudinal movement of the guide wire in the absence of rotation.

53 Claims, 2 Drawing Sheets

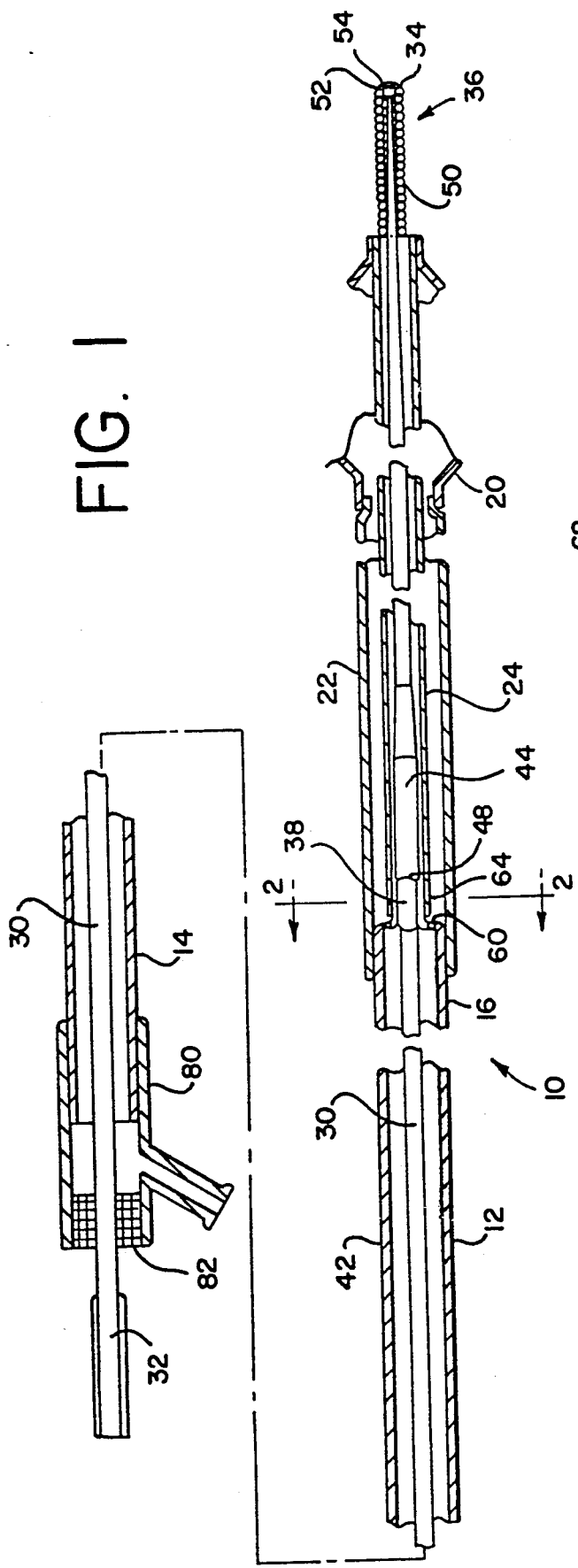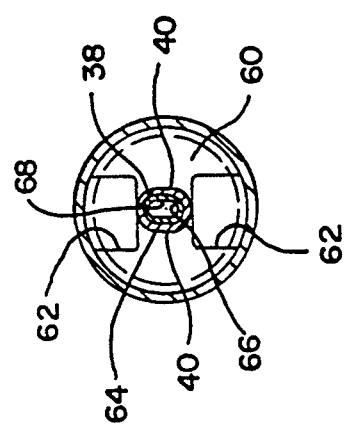

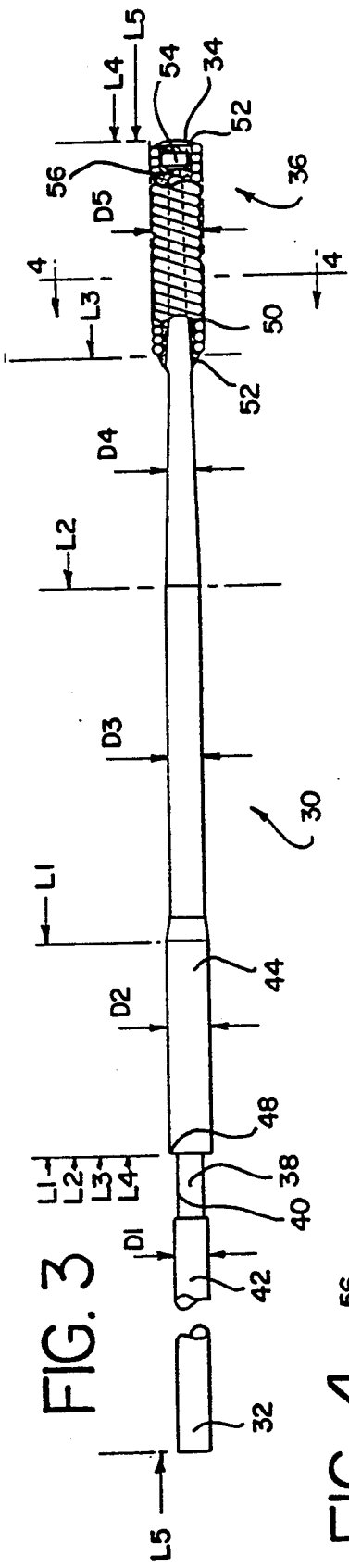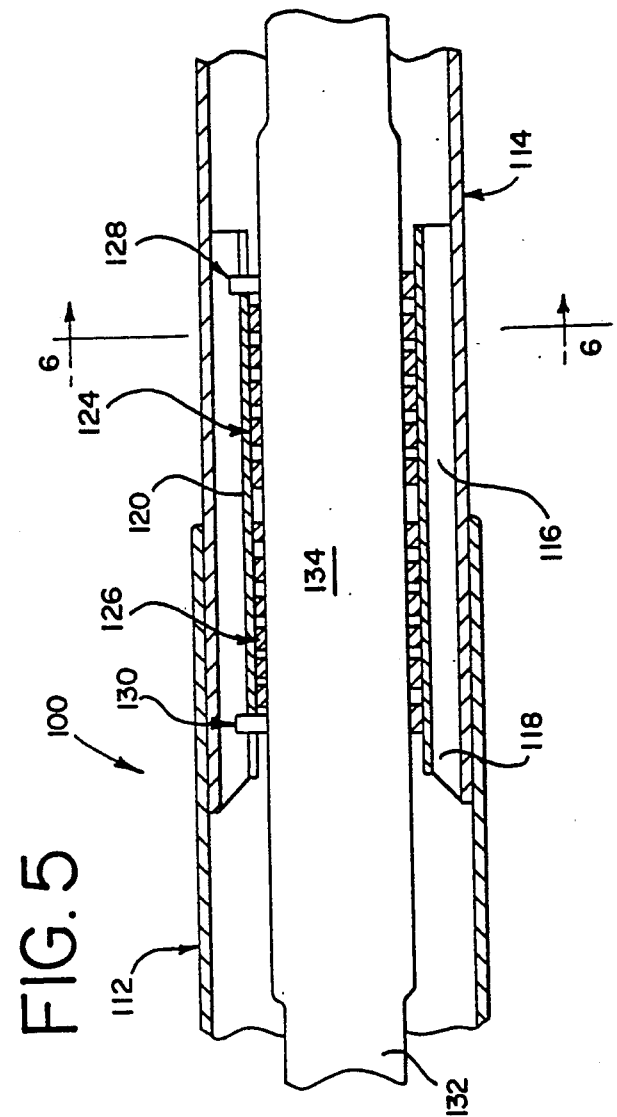

LOW PROFILE CATHETER FOR INCREASING LUMEN SIZE OF A BLOOD VESSEL AND GUIDE WIRE THEREFOR

BACKGROUND OF THE INVENTION

This invention relates to a low profile catheters such as balloon catheters used to increase the lumen size of a blood vessel, and to guide wires used with such catheters.

Catheters such as balloon catheters have been used for some time to increase the lumen size of vessels such as coronary blood vessels. Typically, a flexible guide wire is inserted into a selected vessel, and the guide wire then guides the balloon catheter to the treatment site. Packard U.S. Pat. No. 4,646,742 describes one prior art balloon catheter used in an angioplasty procedure. A coil spring guide wire passes through the catheter, beyond the distal end of the catheter and the balloon. Fogarty U.S. Pat. No. 4,606,347 and Samson U.S. Pat. No. 4,641,654 (FIG. 1b) show other balloon catheters which utilize such guide wires. In the catheter shown in the Fogarty patent a seal is provided near the distal end of the catheter between the catheter and the guide wire.

This prior art approach requires that the guide wire itself be sufficiently rotationally rigid to transmit rotation from its proximal to distal ends when it is rotated to steer the distal end of the guide wire into a desired vessel. As catheters and guide wires are designed for use with increasingly smaller diameter blood vessels, it may be difficult to ensure that the wire has an adequately small diameter yet is adequately torsionally rigid.

Another approach of the prior art is illustrated in the systems described in Mar U.S. Pat. No. 4,771,778, Mar U.S. Pat. No. 4,793,350, Samson U.S. Pat. No. 4,582,181, and Samson U.S. Pat. No. 4,641,654 (FIG. 1a). In these catheters the guide wire is secured to the distal end of the catheter, distally of the balloon, such that a fixed length of the guide wire extends beyond the distal end of the catheter. With this approach, the guide wire is formed as a permanent part of the catheter, and it is therefore not possible to remove the catheter from the blood vessel without simultaneously removing the guide wire. In certain medical procedures it is preferred to leave the guide wire in place at the treatment site while a first catheter is removed from the guide wire. Then a second catheter, possibly different in shape or function from the first, can be guided by the guide wire back to the original treatment site quickly and reliably. Of course, such procedures cannot be performed with a catheter in which the guide wire is permanently affixed to the catheter.

Horzewski U.S. Pat. No. 4,932,959 discloses a vascular dilation catheter which receives a removable guide wire. The catheter shaft defines an annular portion which may be inflated to releasably secure the catheter to the guide wire to allow the two to be advanced as a single unit. The torque transmitting characteristics of the annular inflatable portion are not discussed. However, it is clear that the inflatable portion must be inflated from the distal end of the catheter to secure the catheter to the guide wire and then deflated from the distal end of the catheter to release the catheter from the guide wire. The time required to inflate and deflate the annular portion may limit the speed with which the guide wire can be shifted between the secured and released modes of use.

Accordingly, it is an object of this invention to provide an improved low profile catheter for increasing the lumen size of a blood vessel, which utilizes the catheter shaft to transmit torque to the guide wire at a point near the distal end of the guide wire.

It is another object of this invention to provide such a catheter in which torque is transmitted from the catheter shaft to the guide wire while permitting relative axial movement therebetween.

It is another object of this invention to provide such a catheter in which torque is automatically transmitted from the catheter to the guide wire when the catheter is rotated with respect to the guide wire, and wherein the guide wire is automatically permitted to move longitudinally when the guide wire is advanced with respect to the catheter.

It is yet another object of this invention to provide such a catheter in which the guide wire is shaped to allow the catheter to be removed from the guide wire, in order to allow the guide wire to be left in place at the treatment site while the first catheter is removed and replaced with a second.

SUMMARY OF THE INVENTION

According to this invention a low profile catheter is provided for increasing lumen size of a blood vessel. This catheter includes a catheter shaft having proximal and distal ends and defining an axis extending therebetween. Means are carried by the distal end of the shaft for increasing lumen size of a blood vessel in which the catheter shaft is positioned. A guide wire is positioned in the catheter shaft so as to extend beyond the distal end of the catheter shaft and the lumen size increasing means. Means are provided for automatically transmitting torque from the catheter shaft to the guide wire when the catheter shaft is rotated with respect to the guide wire and for automatically permitting relative axial movement therebetween when the guide wire is advanced with respect to the catheter shaft.

In the preferred embodiments described below the lumen size increasing means comprises an inflatable balloon. Of course, those skilled in the art will recognize that other types of lumen size increasing means can be used, such as atherectomy devices that rely on ablation techniques (light, ultrasonic or hydraulic) or cutting elements of various types.

In the first preferred embodiment described below the torque transmitting means comprises a sleeve carried by the catheter shaft that defines an other than round opening, and a keyed portion of the guide wire shaped to fit into the other than round opening in such a way that the guide wire is slidable in the sleeve, yet the guide wire receives torque via the sleeve from the catheter shaft itself. Because the catheter shaft is of relatively larger diameter than the guide wire, the catheter shaft is well suited to transmit torque from its proximal end to the torque transmitting means.

In the second preferred embodiment described below the torque transmitting means comprises a pair of coil springs configured to seize the guide wire when the catheter shaft is rotated and to allow axial movement of the guide wire in the absence of rotation of the catheter shaft.

This invention is also directed to the low profile dilation catheter and to the keyed guide wire as separate elements.

The invention itself, together with further objects and attendant advantages, will best be understood by reference to the following detailed description, taken in conjunction with the accompanying drawings.

BRIEF DESCRIPTION OF THE DRAWINGS

FIG. 1 is a longitudinal sectional view in partial cutaway of a low profile catheter assembly which incorporates a first presently preferred embodiment of this invention.

FIG. 2 is a cross-sectional view taken along line 2—2 of FIG. 1.

FIG. 3 is a fragmentary side view in partial cutaway of the guide wire included in the catheter assembly of FIG. 1.

FIG. 4 is a cross-sectional view taken along line 4—4 of FIG. 3.

FIG. 5 is a longitudinal sectional view of portions of a low profile catheter assembly which incorporates a second preferred embodiment of this invention.

FIG. 6 is a cross sectional view taken along line 6—6 of FIG. 5.

DETAILED DESCRIPTION OF THE PRESENTLY PREFERRED EMBODIMENTS

Turning now to the drawings, FIG. 1 shows a longitudinal sectional view of a low profile catheter assembly 10. The catheter assembly 10 includes a catheter having a catheter shaft 12 which defines a proximal end 14 and a distal end 16. In this embodiment, the catheter shaft 12 is torsionally rigid and is formed of a ferrous metal alloy.

The distal end 16 of the shaft 12 carries a means for increasing the lumen size of a blood vessel in which the shaft 12 is placed. In this embodiment, the lumen size increasing means includes an inflatable balloon 20 which is sealed at its proximal end to an outer tube 22 and at its distal end to an inner tube 24. The outer tube 24 is in turn sealed to the distal end of the shaft 12. The inner tube 24 extends axially through the balloon 20 and is sealed at its proximal end to a necked down portion of the shaft 12. As pointed out above, this invention is not limited to use with balloon type lumen size increasing means. Rather, it can also be adapted for use with other means for performing this function, such as devices including lasers or cutting, scraping or abrading edges.

Simply by way of example, in this preferred embodiment the inner tube 24 is formed of high density polyethylene and has an outer diameter of 0.016 inch and a wall thickness of 0.0025 inch. The balloon 20 can be formed of any conventional material such as a polyolefin copolymer in a thickness of 0.001-0.003 inches, depending on balloon diameter, and the outer tube 22 can be formed of a material such as high density polyethylene having an outer diameter of 0.026 inch and a wall thickness of 0.003 inch. The shaft 12 can be formed from 304 stainless steel with an outer diameter of 0.026 inch and a wall thickness of 0.0035 inch.

FIGS. 1 and 3 show two views of a guide wire 30 that is mounted inside the shaft 12 as part of the catheter assembly 10. The guide wire 30 defines a proximal end 32 and a distal end 34. The distal end 34 forms a flexible end portion 36 that is configured to follow a blood vessel without damaging the walls of the vessel.

Intermediate the proximal and distal ends, the guide wire 30 defines a keyed portion 38 which defines a pair of opposed flats 40 as shown in FIG. 2. The keyed portion 38 is positioned in FIG. 1 near the distal end 16 of the shaft 12. The guide wire 30 defines a region 42 extending proximally of the keyed portion 38 to the proximal end 32. This region 42 is sized no larger than the keyed portion 38, and in this embodiment is of reduced diameter as compared with the keyed portion 38. The guide wire 30 defines an enlarged region 44 which is positioned immediately distally of the keyed portion 38. The transition between the enlarged region 44 and the keyed portion 38 is formed by transverse shoulder 48. The maximum diameter of the guide wire 30 is defined at the flexible end portion 36. This flexible end portion 36 includes a coil spring 50 which is brazed at each end to the guide wire 30 as indicated at reference numeral 52. The distal end 34 of the guide wire 30 defines an enlarged end 54 sized to fit within the coil spring 50. Proximally of the enlarged end 54 is a neck region 56, shaped as shown in FIG. 4.

In this preferred embodiment the guide wire 30 is formed of a solid main wire which can be formed of a ferrous alloy such as 304 stainless steel. The coil spring 50 can for example be formed of a radiopaque wire having a diameter of 0.002 inches. Simply to define the presently preferred embodiment of this invention, the following table lists preferred dimensions for the diameters D1–D5 and the lengths L1–L5, as shown in FIG. 3:

| MEASUREMENT | PREFERRED DIMENSION (inches) |
| --- | --- |
| D1 | 0.008 |
| D2 | 0.0095 |
| D3 | 0.0078 |
| D4 | 0.0055 |
| D5 | 0.100 |
| L1 | 4.00 |
| L2 | 7.00 |
| L3 | 11.00 |
| L4 | 11.93 |
| L5 | 69. (175 cm) |

The flats 40 in this embodiment have an axial length of 15 cm, though flats 40 may also be used which are less than 10 cm in length.

The catheter 10 includes means for transmitting torque from the shaft 12 to the guide wire 30 and allowing axial movement therebetween. In this preferred embodiment, the torque transmitting means is implemented as a keyed sleeve 64 which is secured to the distal end of the shaft 12 by a transversely oriented plate 60. In the embodiment shown in FIG. 1 the plate 60 and the sleeve 64 are integrally formed with the shaft 12. Of course, this detail of construction is not to be considered as an essential feature of this invention, and multiple pieces can be secured together to achieve the same function.

As shown in FIG. 2, the plate 60 defines two openings 62 which are provided to pass an inflating fluid between the interior of the shaft 12 and the balloon 20. The sleeve 64 defines an interior opening 66 which is other than round in cross section. The opening 66 defines a pair of flats 68 which are shaped to engage the flats 40 so as to prevent relative rotation between the shaft 12 and the guide wire 30. The fit between the keyed portion 38 of the guide wire 30 and the opening 66 of the sleeve 64 is a sliding fit that allows the guide wire 30 to be moved axially with respect to the catheter shaft 12. Nevertheless, because of the mating engagement of the flats 68, 40 rotational forces applied to the proximal end 14 of the shaft 12 are applied via the sleeve 64 and the keyed portion 38 to the guide wire 30 at a point near the distal end 34 of the guide wire 30. The shoulder 48 is shaped to engage the distal end of the sleeve 64 to provide a positive stop. Thus, by moving the guide wire 30 until the shoulder 48 contacts the sleeve 64, it can be ensured that the sleeve 64 is in torque transmitting engagement with the keyed portion 38 of the guide wire 30.

An inflation manifold 80 is secured to the proximal end 14 of the shaft 12 to accommodate introduction of an inflating fluid into the interior of the shaft 12. This inflation manifold 80 can be connected in a conventional manner to a source of pressurized inflating fluid (not shown) when the balloon 20 is to be inflated. The inflation manifold 80 also functions as a means for applying torque to the proximal end 14 of the shaft 12. In use, the inflation manifold 80 can be rotated to rotate the shaft 12 and thereby apply rotating torques to the keyed portion 38 of the guide wire 30. A seal 82 is provided on the inflation manifold 80 to prevent the release of inflating fluid around the guide wire 30. This seal 82 accommodates relative axial movement between the guide wire 30 and the shaft 12.

In use, the distal end 34 of the guide wire 30 is provided with a prebent curvature (not shown), and the guide wire 30 is assembled with the shaft 12 as shown in FIG. 1. This assembly is then inserted in the conventional manner into the vascular system of a patient. The guide wire 30 is used to guide the balloon 20 into the desired arterial branch. This is done by advancing the distal end 34 of the guide wire 30 into the desired arterial branch. When rotation is required to orient the prebent distal end 34, the shaft 12 is positioned to engage the sleeve 64 with the keyed portion 38, and then the inflation manifold 80 is manually rotated. The shaft 12 is torsionally rigid as explained above, and rotational movement applied to the proximal end 14 is transmitted substantially completely to the distal end 16, where it is applied to the keyed portion 38 of the guide wire 30. The portion of the guide wire 30 between the keyed portion 38 and the distal end 34 has sufficient torsional rigidity to rotate the distal end 34 of the guide wire 30 smoothly and reliably. In this embodiment the coil spring 50 is formed of a radiopaque alloy including a metal such as platinum to allow the position of the coil spring 50 to be visualized on a flouriscope during the steering operation.

In this way, the shaft 12 and guide wire 30 cooperate to provide an easily steerable guide wire 30 which is nevertheless extremely small in diameter. Because the shaft 12 itself transmits torque to the keyed portion 38, the torsional rigidity of the guide wire proximal to the keyed portion 38 may be low with-out interfering with the ease with which the distal end 34 may be rotated and steered. Thus, this invention has particular advantages in extremely small diameter catheters which by necessity require even smaller diameter guide wires (less than 0.020 inches in diameter), which may not be well suited to transmit torques effectively over a length of more than 150 cm. In the preferred embodiment described above the keyed region 38 is positioned approximately 12 inches proximally of the distal end 34. The overall length of the guide wire 30 is 175 cm or about 69 inches. Thus, the keyed portion 38 is spaced from the distal end 34 by no more than about 20 percent of the overall length of the guide wire 30.

The catheter 10 provides the important advantage that once the guide wire 30 has been used to advance the balloon 20 to a desired treatment site, the shaft 12 and the balloon 20 can be removed from the proximal end 32 of the guide wire 30, while leaving the guide wire 30 in place in the treatment site. This is possible because the region 42 proximal to the keyed portion 38 is sized to fit through the sleeve 64. Once the shaft 12 has been removed from the guide wire 30, a second catheter, which may or may not be similar to the catheter shown in FIG. 1, may be advanced along the guide wire 30 directly to the original treatment site. Conventional extension wires may be used to facilitate the exchange. Alternately, the catheter may be designed such that the guide wire extends outside the catheter for the proximal portion of the catheter and is received into the catheter for only the distal 15–30 cm of the catheter.

FIGS. 5 and 6 show portions of a second preferred embodiment of the catheter assembly of this invention. This embodiment includes a catheter 100 having a shaft that comprises a proximal tube 112 and a distal tube 114 which are rigidly secured together at a point about 11 cm from the distal end of the catheter 100 (at approximately the position of the plate 60 in the catheter 10). The proximal end of the proximal tube 112 is secured to an inflation manifold (not shown) similar to the inflation manifold 80. Similarly, the distal end of the distal tube 114 carries a balloon (not shown) similar to the balloon 30.

As shown in FIGS. 5 and 6, a spring carrier spyder 116 is fixed to the distal tube 114, as for example by welding. The spyder defines four fins 118 which support a tube 120 coaxially with the tube 114. The region between the tubes 120, 114 forms four flow passages 122 that allow an inflation fluid to pass between the proximal and distal tubes 112, 114 for inflation of the balloon (not shown).

Two coil springs 124, 126 are mounted within the tube 120, each fixed at one end by a respective spring tab 128, 130 which is securely fixed in place on the tube 120. Both of the springs 124, 126 are formed of rectangular section spring wire, and they are wound in the same direction.

A guide wire 132 is positioned within the springs 124, 126, and the guide wire 132 may be configured at its proximal and distal ends (not shown) like the guide wire 30. The guide wire 132 defines an enlarged cylindrical portion 134 which in this embodiment is at least 10 and preferably 15 cm in length. The enlarged cylindrical portion 134 is sized to allow the catheter 100 to be removed from the proximal end of the guide wire 132 and to move longitudinally through the springs 124, 126 freely in the absence of relative rotation between the catheter 100 and the guide wire 132. However, when the catheter 100 is rotated in either direction with respect to the guide wire 132, the respective one of the springs 124, 126 automatically grips the guide wire 132 to prevent any relative rotation between the catheter 100 and the guide wire 132. Right hand rotation of the catheter 100 with respect to the guide wire 132 winds up the spring 124 and causes the spring 124 to seize the guide wire 132. Similarly, left hand rotation of the catheter 100 with respect to the guide wire 132 winds up the spring 126 and causes the spring 126 to seize the guide wire 132. In the absence of rotation of the catheter in either direction, both of the springs 124, 126 automatically relax, thereby automatically freeing the guide wire for longitudinal movement in the catheter 100.

The catheter 100 and guide wire 132 can be used as described above such that the torsional rigidity of the catheter 100 applies torque to the guide wire 132 near the distal end of the guide wire 132.

Simply by way of example, in this preferred embodiment the proximal tube 112 is formed of polyethylene, and the distal tube 114 is a stainless steel hypotube. Preferably, the spring carrier spyder is also formed of stainless steel.

Of course, it should be understood that a wide range of changes and modifications can be made to the preferred embodiment described above. As explained above, atherectomy devices or lasers may be used instead of the balloon 20 as a lumen size increasing means. Additionally, the torque transmitting means does not necessarily include opposed flats as described above. Rather, a wide range of geometries can be used as long as they achieve the dual purposes of allowing relative axial movement and transmitting torque. Additionally, the distal end of the guide wire 30 can be altered in configuration and components as desired. Of course, materials and dimensions can be modified as desired to suit the intended application.

It is therefore intended that the foregoing detailed description be regarded as illustrative rather than limiting, and that it be understood that it is the following claims, including all equivalents, which are intended to define the scope of this invention.

What is claimed is:

1. A low profile catheter for increasing lumen size of a blood vessel, comprising:
   a catheter shaft having proximal and distal ends and defining an axis extending therebetween;
   first means, carried by the distal end of the shaft, for increasing lumen size of a blood vessel in which the catheter shaft is positioned;
   a guide wire positioned in the catheter shaft, said guide wire having proximal and distal ends, said distal en extending beyond the distal end of the catheter shaft and the lumen size increasing means; and
   second means for automatically transmitting torque from the catheter shaft to the guide wire when the catheter shaft is rotated with respect to the guide wire and for automatically permitting relative axial movement therebetween when the guide wire is advanced with respect to the catheter shaft said second means located in said catheter shaft at least in part adjacent to said guide wire.

2. The invention of claim 1 wherein the second means is carried by the catheter shaft near the distal end of the catheter shaft, proximally of the lumen size increasing means.

3. The invention of claim 1 wherein the guide wire defines a keyed portion shaped to engage the second means.

4. The invention of claim 1 wherein the second means comprises a keyed coupling member carried by the catheter shaft and shaped and positioned to receive the keyed portion of the guide wire.

5. The invention of claim 1 wherein the first means comprises an inflatable balloon.

6. The invention of claim 1 wherein the guide wire has a length, and wherein the second means is configured to transmit torque to the guide wire at a point spaced from the distal end of the guide wire by no more than 20% of the length.

7. The invention of claim 6 wherein the catheter shaft comprises a solid wall tube formed of a ferrous metal alloy.

8. The invention of claim 6 wherein the guide wire has a maximum diameter no greater than about 0.010 inches and a length no less than about 150 cm.

9. The invention of claim 1 further comprising means, secured to the proximal end of the catheter shaft, for applying torque to the catheter shaft.

10. The invention of claim 3 wherein the keyed portion extends over a length of at least 10 cm to permit at least 10 cm of relative axial movement between the guide wire and the catheter shaft while retaining torque transmitting engagement between the catheter shaft and the guide wire.

11. The invention of claim 1 wherein a proximal portion of the guide wire is sized and shaped to pass through the second means to permit the catheter shaft and the first means to be removed from the proximal end of the guide wire.

12. The invention of claim 1 wherein the second means comprises at least one coil spring carried by the catheter shaft and shaped and positioned to automatically seize the guide wire for rotation with the catheter shaft when the catheter shaft is rotated in a first direction with respect to the guide wire by winding of the spring.

13. The invention of claim 12 wherein the at least one coil spring comprises two coil springs, each shaped and positioned to automatically seize the guide wire for rotation with the catheter shaft when the catheter shaft is rotated in a respective direction with respect to the guide wire.

14. A low profile dilation catheter comprising:
   a catheter shaft having proximal and distal ends and defining an axis extending therebetween;
   an inflatable balloon carried by the distal end of the catheter shaft;
   a guide wire positioned in the catheter shaft, said guide wire having proximal and distal ends, said distal end extending beyond the distal end of the catheter shaft and through the balloon, said guide wire defining a keyed portion having a cross sectional shape which is other than round; and
   a keyed coupling member carried by the catheter shaft and coupled to the keyed portion of the guide wire, said keyed coupling member operative to transmit torque from the catheter shaft to the guide wire while permitting relative axial movement between the catheter shaft and the guide wire.

15. The invention of claim 14 wherein the coupling member is positioned at the distal end of the catheter shaft, proximal to the balloon.

16. The invention of claim 14 wherein the keyed portion extends over a length of at least 10 cm to permit at least 10 cm of relative axial movement between the guide wire and the catheter shaft while retaining torque transmitting engagement between the catheter shaft and the guide wire.

17. The invention of claim 14 wherein the guide wire proximal to the keyed portion is sized and shaped to pass through the coupling member to permit the catheter shaft and balloon to be removed from the proximal end of the guide wire.

18. The invention of claim 14 wherein the coupling member comprises:
   a plate extending radially inwardly from the distal end of the catheter shaft; and
   a sleeve positioned centrally of said catheter shaft at the distal end of the catheter shaft by the plate, said sleeve defining an other than round opening sized to receive the keyed portion of the guide wire to transmit torque to the guide wire while permitting relative axial movement between the sleeve and the guide wire.

19. The invention of claim 18 wherein the plate is positioned proximally of the balloon within the catheter shaft, and wherein the plate defines at least one opening positioned to pass an inflating fluid between the catheter shaft and the balloon.

20. The invention of claim 14 further comprising means, secured to the proximal end of the catheter shaft, for applying torque to the catheter shaft.

21. The invention of claim 14 wherein the guide wire defines an enlarged portion located distally of the keyed portion and sized to prevent the enlarged portion from passing through the coupling member.

22. The invention of claim 18 further comprising a tube extending at least in part through the balloon and secured to the distal end of the sleeve to pass through the balloon, said tube receiving the guide wire and conducting the guide wire distally of the balloon.

23. The invention of claim 14 wherein the catheter shaft is torsionally rigid.

24. The invention of claim 14 wherein the catheter shaft comprises a solid wall tube formed of a ferrous metal alloy.

25. The invention of claim 14 wherein the guide wire has a maximum diameter no greater than about 0.010 inches and a length no less than about 150 cm.

26. The invention of claim 14 wherein the guide wire has a length, and wherein the coupling member is positioned to transmit torque to the guide at a point spaced from the distal end of the guide wire by no more than about 20% of the length.

27. A low profile dilation catheter comprising:
a catheter shaft having proximal and distal ends and defining an axis extending therebetween;
a sleeve carried by the caterer shaft and having an internal opening extending along the shaft and which is other than round;
means, carried by the distal end of the catheter shaft, for increasing lumen size of a blood vessel in which the catheter shaft is positioned;
said sleeve operative to receive a guide wire axially movable in the sleeve and to transmit torque thereto;
said lumen size increasing means configured to pass the guide wire distally thereof.

28. The invention of claim 27 wherein the lumen size increasing means comprises an inflatable balloon.

29. The invention of claim 27 wherein the sleeve is positioned at the distal end of the catheter shaft.

30. The invention of claim 28 wherein the sleeve is positioned at the distal end of the catheter shaft, and wherein the sleeve is secured to the catheter shaft by a support member which is provided with at least one opening for passing an inflating fluid between the catheter shaft and the balloon.

31. The invention of claim 27 further comprising means, secured to the proximal end of the catheter shaft, for applying torque to the catheter shaft.

32. The invention of claim 28 further comprising a tube secured to the distal end of the sleeve and passing through the balloon to conduct a guide wire distally thereof.

33. The invention of claim 27 wherein the catheter shaft is torsionally rigid.

34. The invention of claim 27 wherein the catheter shaft comprises a solid wall tube formed of a ferrous metal alloy.

35. A guide wire for a low profile catheter for increasing lumen size of a blood vessel, said guide wire comprising:
a wire body having a proximal end and a distal end;
a flexible end portion carried by the wire body at the distal end;
said wire body forming a region near the distal end, said region having a cross section which is other than round;
said wire body having a maximum diameter less than 0.020 inches.

36. The invention of claim 35 wherein the keyed region has a length greater than 10 cm.

37. The invention of claim 35 wherein the maximum diameter is located distally region.

38. The invention of claim 35 wherein the wire body proximal to the region is sized no larger than the region.

39. The invention of claim 38 wherein the wire body distal to the region is at least in part larger in cross section than the region.

40. The invention of claim 35 wherein the region is substantially constant in cross sectional shape over a distance of at least about 10 cm.

41. The invention of claim 35 wherein the wire body has a maximum diameter no greater than about 0.010 inches and a length no less than about 150 cm.

42. The invention of claim 41 wherein the region extends to a point separated from the end portion by no more than about 20% of the length of the wire body.

43. A low profile catheter for increasing lumen size of a blood vessel, comprising:
a catheter shaft having proximal and distal ends and defining an axis extending therebetween;
first means, carried by the distal end of the shaft, for increasing lumen size of a blood vessel in which the catheter shaft is positioned;
a guide wire positioned in the catheter shaft, said guide wire having proximal and distal ends, said distal end extending beyond the distal end of the catheter shaft and the lumen size increasing means; and
a first coil spring carried by the catheter shaft and positioned to surround the guide wire, said first coil spring operative to seize the guide wire for rotation with the catheter shaft when the catheter shaft is rotated in a first direction with respect to the guide wire, and to release the guide wire for longitudinal movement with respect to the catheter shaft when the catheter shaft is not rotated in the first direction with respect to the guide wire.

44. The invention of claim 43 wherein the first coil spring is carried by the catheter shaft near the distal end of the catheter shaft, proximally of the lumen size increasing means.

45. The invention of claim 43 wherein the first means comprises an inflatable balloon.

46. The invention of claim 43 wherein the guide wire has a length, and wherein the coil spring is positioned in the catheter shaft to transmit torque to the guide wire at a point spaced from the distal end of the guide wire by no more than 20% of the length.

47. The invention of claim 43 wherein the guide wire defines a cylindrical portion sized to engage the first coil spring, wherein the cylindrical portion has a length of at least about 10 cm.

48. The invention of claim 43 wherein a proximal portion of the guide wire is sized and shaped to pass through the first coil spring to permit the catheter shaft and the first means to be removed from the proximal end of the guide wire.

49. The invention of claim 43 further comprising a second coil spring carried by the catheter shaft and positioned to surround the guide wire, said second coil spring operative to seize the guide wire for rotation with the catheter shaft when the catheter shaft is rotated in a second direction with respect to the guide wire, and to release the guide wire for longitudinal movement with respect to the catheter shaft when the catheter shaft is not rotated in the second direction with respect to the guide wire, wherein the first and second directions are oppositely directed.

50. A low profile catheter for increasing lumen size of a blood vessel, comprising:
 a catheter shaft having proximal and distal ends and defining an axis extending therebetween;
 means, carried by the distal end of the shaft, for increasing lumen size of a blood vessel in which the catheter shaft is positioned;
 a first spring carried by the catheter shaft and wound in a selected direction, said first coil spring operative to receive a guide wire which is axially movable in the first coil spring in the absence of rotation of the catheter shaft in a first direction, and to seize the guide wire for rotation with the catheter shaft when the catheter shaft is rotated in the first direction with respect to the guide wire.

51. The invention of claim 50 wherein the lumen size increasing means comprises an inflatable balloon.

52. The invention of claim 50 wherein the spring is positioned near the distal end of the catheter shaft.

53. The invention of claim 50 further comprising a second coil spring carried by the catheter shaft and positioned to surround the guide wire, said second coil spring operative to seize the guide wire for rotation with the catheter shaft when the catheter shaft is rotated in a second direction with respect to the guide wire, and to release the guide wire for longitudinal movement with respect to the catheter shaft when the catheter shaft is not rotated in the second direction with respect to the guide wire, wherein the first and second directions are oppositely directed.

* * * * *

UNITED STATES PATENT AND TRADEMARK OFFICE
CERTIFICATE OF CORRECTION

PATENT NO. : 5,195,989
DATED : March 23, 1993
INVENTOR(S) : Charles L. Euteneuer Page 1 of 2

It is certified that error appears in the above-indentified patent and that said Letters Patent is hereby corrected as shown below:

In column 1, line 8, before "low" delete "a".

In column 5, line 58, before "which", insert --preferably less than .012 diameter,--.

Column 7:
    In claim 1, line 10, before "extending" delete "en".
    In claim 4, line 1, delete "1" and substitute therefor --3--.

Column 9: In claim 27, line 4, delete "caterer".

Column 10, claim 36, line 1, delete "keyed".

UNITED STATES PATENT AND TRADEMARK OFFICE
CERTIFICATE OF CORRECTION

PATENT NO. : 5,195,989
DATED : March 23, 1993
INVENTOR(S) : Charles L. Euteneuer It is certified that error appears in the above-indentified patent and that said Letters Patent is hereby corrected as shown below:

Column 10:
In claim 37, line 2, before "region" insert --of the--.

Column 1, line 8, before "low" delete "a".
Column 5, line 58, before "which", insert --preferably less than .012 diameter."
Column 7, line 37, claim 1, before "extending" delete "en", insert --end--.
Column 7, line 55, claim 4, delete "1" and substitute therefore--"3"--.
Column 9, line 39, claim 27, delete "caterer", insert --catheter--.
Column 10, line 15, claim 36, delete "keyed".
Column 10, line 2, claim 37, before "region" insert --of the --.

Signed and Sealed this

Twenty-eighth Day of June, 1994

Attest:

BRUCE LEHMAN

*Attesting Officer*  *Commissioner of Patents and Trademarks*